(12) United States Patent
Baldini et al.

(10) Patent No.: US 9,265,469 B2
(45) Date of Patent: Feb. 23, 2016

(54) DEVICE FOR THE ACQUISITION OF PANORAMIC RADIOGRAPHIES AND CBCT VOLUMETRIC RADIOGRAPHIES

(75) Inventors: Antonio Baldini, Imola (IT); Davide Bianconi, Castel Guelfo di Bolonga (IT); Antonio Becca, Imola (IT)

(73) Assignee: CEFLA SOCIETA COOPERATIVA, Imola (IT)

(*) Notice: Subject to any disclaimer, the term of this patent is extended or adjusted under 35 U.S.C. 154(b) by 534 days.

(21) Appl. No.: 13/596,321

(22) Filed: Aug. 28, 2012

(65) Prior Publication Data

US 2013/0089177 A1 Apr. 11, 2013

(30) Foreign Application Priority Data

Oct. 5, 2011 (IT) .............................. BO2011A0566

(51) Int. Cl.
*A61B 6/14* (2006.01)
*A61B 6/00* (2006.01)
*A61B 6/03* (2006.01)

(52) U.S. Cl.
CPC .................. *A61B 6/14* (2013.01); *A61B 6/4266* (2013.01); *A61B 6/032* (2013.01)

(58) Field of Classification Search
CPC ......... A61B 6/14; A61B 6/032; A61B 6/4266
USPC ............................................. 378/13, 29, 38
See application file for complete search history.

(56) References Cited

U.S. PATENT DOCUMENTS

| | | | |
|---|---|---|---|
| 3,673,408 A | 6/1972 | Moss | |
| 4,323,779 A | 4/1982 | Albert | |
| 4,443,191 A | 4/1984 | Gutierrez | |
| 5,016,264 A * | 5/1991 | Hyttinen | 378/38 |
| 5,500,884 A * | 3/1996 | Guenther et al. | 378/38 |
| 5,511,106 A | 4/1996 | Doebert et al. | |
| 5,995,583 A | 11/1999 | Schick et al. | |
| 6,081,739 A | 6/2000 | Lemchen | |
| 6,614,875 B2 * | 9/2003 | Suuronen | 378/63 |
| 6,829,326 B2 | 12/2004 | Woods et al. | |
| 7,092,483 B2 | 8/2006 | Nyholm | |
| 7,322,746 B2 | 1/2008 | Beckhaus et al. | |
| 7,424,091 B2 | 9/2008 | Park et al. | |
| 7,486,759 B2 | 2/2009 | Suzuki et al. | |
| 7,534,038 B2 * | 5/2009 | Rotondo et al. | 378/205 |
| 7,559,692 B2 | 7/2009 | Beckhaus et al. | |

(Continued)

FOREIGN PATENT DOCUMENTS

| | | |
|---|---|---|
| EP | 1752099 | 11/2005 |
| EP | 2156791 | 8/2009 |

(Continued)

OTHER PUBLICATIONS

Sherman, R., "Teleradiography: Extending the focus film distance" The Journal of the CCA vol. 30 No. 3 (1986).*

(Continued)

*Primary Examiner* — Wyatt Stoffa
(74) *Attorney, Agent, or Firm* — Cooper & Dunham LLP

(57) ABSTRACT

An extraoral dental radiographic apparatus which performs panoramic radiographies, cone beam volumetric radiographies of the facial skeleton and cranial teleradiographies. An alternating mechanism brings x-ray sensors toward the x-ray radiation source, such that the sensor axes intersect at an angle.

13 Claims, 4 Drawing Sheets

(56) References Cited

U.S. PATENT DOCUMENTS

| | | |
|---|---|---|
| 7,715,525 B2 | 5/2010 | Spartiotis et al. |
| 7,715,526 B2 | 5/2010 | Spartiotis et al. |
| 7,742,560 B2 | 6/2010 | Spartiotis et al. |
| 7,773,720 B2 * | 8/2010 | Honjo et al. ............... 378/19 |
| 7,798,708 B2 | 9/2010 | Erhardt et al. |
| 7,804,933 B2 | 9/2010 | Nyholm |
| 7,961,841 B2 * | 6/2011 | Ro et al. ............... 378/38 |
| 8,005,186 B2 | 8/2011 | Lee |
| 8,005,187 B2 | 8/2011 | Suzuki et al. |
| 8,120,683 B1 | 2/2012 | Tumer et al. |
| 8,144,829 B2 * | 3/2012 | Zhu et al. ............... 378/7 |
| 8,152,373 B2 | 4/2012 | Erhardt et al. |
| 8,306,181 B2 | 11/2012 | Spartiotis et al. |
| 8,588,364 B2 | 11/2013 | Suzuki et al. |
| 9,060,716 B2 | 6/2015 | Bianconi et al. |
| 2003/0161438 A1 | 8/2003 | Woods et al. |
| 2004/0190678 A1 * | 9/2004 | Rotondo et al. ............... 378/38 |
| 2006/0227934 A1 | 10/2006 | Beckhaus et al. |
| 2006/0233301 A1 | 10/2006 | Erhardt et al. |
| 2007/0030951 A1 * | 2/2007 | Park et al. ............... 378/38 |
| 2008/0130831 A1 * | 6/2008 | Rotondo et al. ............... 378/38 |
| 2008/0137802 A1 | 6/2008 | Suzuki et al. |
| 2008/0144766 A1 | 6/2008 | Beckhaus et al. |
| 2009/0168966 A1 | 7/2009 | Suzuki et al. |
| 2009/0196395 A1 * | 8/2009 | Gregorio et al. ............... 378/38 |
| 2009/0232274 A1 | 9/2009 | Spartiotis et al. |
| 2009/0232275 A1 | 9/2009 | Spartiotis et al. |
| 2009/0245461 A1 | 10/2009 | Lee |
| 2009/0304148 A1 | 12/2009 | Nyholm |
| 2010/0034340 A1 | 2/2010 | Spartiotis et al. |
| 2010/0128840 A1 * | 5/2010 | Cha ............... 378/4 |
| 2010/0195786 A1 * | 8/2010 | Ro et al. ............... 378/4 |
| 2010/0278299 A1 * | 11/2010 | Loustauneau et al. ........ 378/13 |
| 2010/0303204 A1 * | 12/2010 | Erhardt et al. ............... 378/62 |
| 2011/0064188 A1 | 3/2011 | Suzuki et al. |
| 2011/0150185 A1 | 6/2011 | Uzbelger Feldman |
| 2012/0039436 A1 * | 2/2012 | Bothorel et al. ............... 378/11 |
| 2012/0189096 A1 * | 7/2012 | Erhardt et al. ............... 378/22 |
| 2012/0314835 A1 | 12/2012 | Muller |
| 2012/0321035 A1 | 12/2012 | Muller |
| 2013/0003921 A1 * | 1/2013 | Spartiotis et al. ............... 378/38 |
| 2013/0163718 A1 * | 6/2013 | Lindenberg et al. ............... 378/39 |
| 2013/0307923 A1 | 11/2013 | Inglese et al. |

FOREIGN PATENT DOCUMENTS

| | | |
|---|---|---|
| WO | 9820796 | 5/1998 |
| WO | 2008028988 | 3/2008 |
| WO | 2010128404 | 11/2010 |

OTHER PUBLICATIONS

Italian Patent Office search report and opinion in IT BO20110566.

* cited by examiner

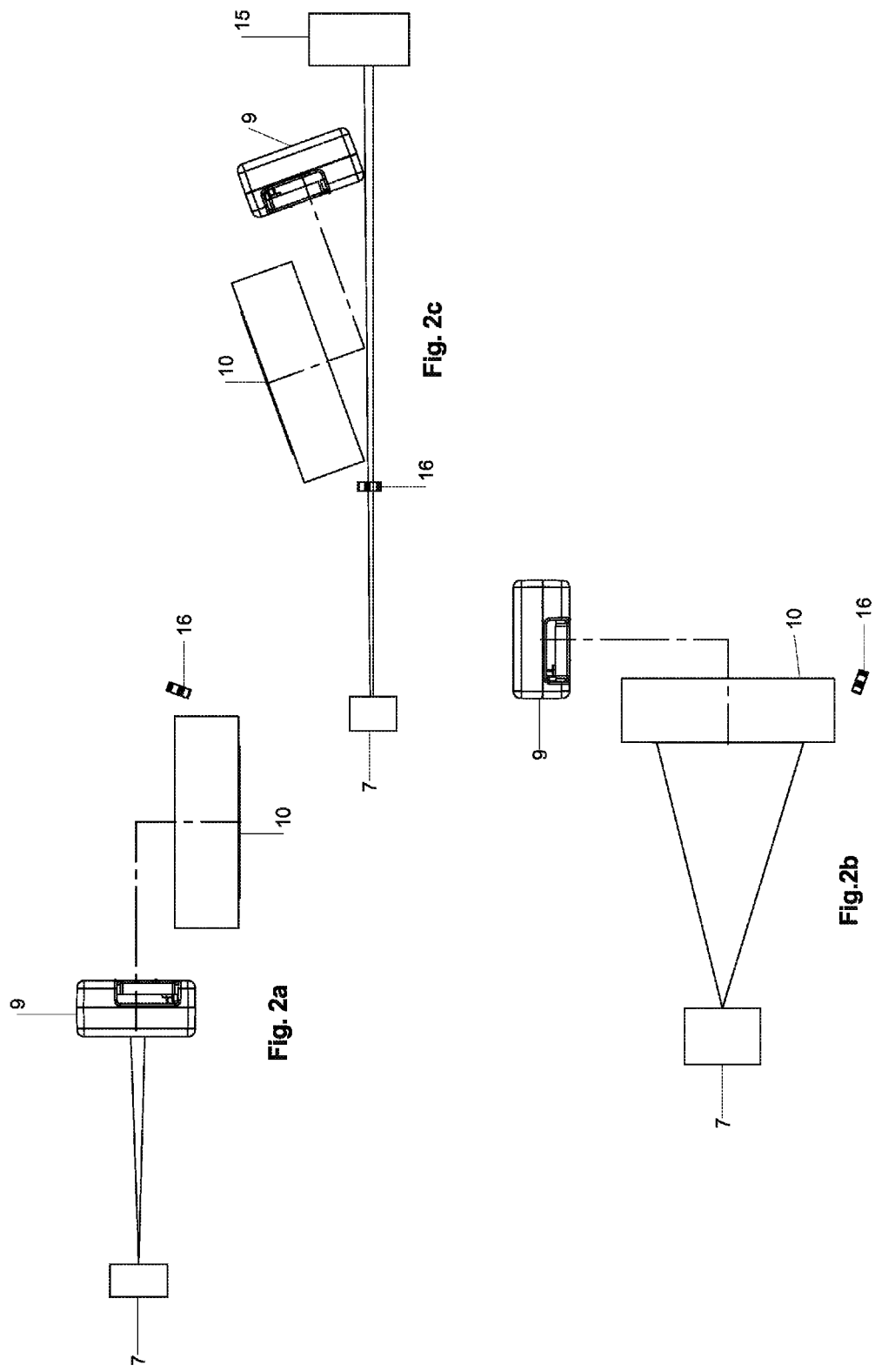

DEVICE FOR THE ACQUISITION OF PANORAMIC RADIOGRAPHIES AND CBCT VOLUMETRIC RADIOGRAPHIES

BACKGROUND OF THE INVENTION

The present invention refers to the technical field of extraoral dental radiography, and particularly to a device alternatively performing panoramic radiographies, cone beam volumetric radiographies of facial skeleton and cranial teleradiographies. All these types of radiographies are well known in the art.

Panoramic radiography (also known as orthopantomography) produces a radiographic image of a curved plan approximating patient jaws, with blurring of the anatomical structures laying outside a narrow layer around the predesigned curved plane.

Cone beam volumetric radiography (also known as CBCT) is the acquisition, from different projection angles, of a series of bidimensional radiographic images which will be processed post-acquisition to reconstruct tridimensional volumes.

Teleradiography is a projective radiographic technique, producing radiographic images of the skull or of other anatomical areas from different projections, with minimum magnification and geometrical distortion. Usually two perspectives are represented, latero-lateral and anteroposterior.

Generally on the market two types of equipment are available: a first type is panoramic equipment, alternatively performing panoramic radiographies and teleradiographies, and a second type dedicated to CBCT volumetric radiography. These equipments are expensive and cumbersome.

BRIEF SUMMARY OF THE INVENTION

Aim of the present invention is providing an X-ray imager alternatively performing, after appropriate setting up of the X-ray imager, said three types of radiologic examination, and which can be easily and cheaply produced.

The X-ray imager according to the present invention has an X-ray source and different X-ray sensors, of the type appropriate for the examination to be performed, arranged at an appropriate distance from the X-ray source so that good-quality images can be obtained. The X-ray source is the same for the three types of radiographic acquisition.

In particular, the invention consists in the respective disposition of the panoramic (PAN) and the cone beam volumetric radiography (CBCT) sensors, which are respectively arranged to form an angle.

In the choice of the angle between PAN sensor and CBCT sensor different issues have to be accounted for: X-ray imager set up rapidity, temperature, and protection from non-collimated X-rays.

The shortest X-ray imager set up time for the specific acquisition is desirable: a small angle between the two sensors would accelerate their exchange.

When the sensor is active, and especially when it has to acquire and transmit a great number of signals, as it is needed in this type of application, heat is produced: this would lead to the longest possible distance between PAN sensor and CBCT sensor, with the aim of an efficient heat removal.

When X-rays are emitted from the X-ray source, a small quantity of rays might hit outside the sensor's sensitive area, potentially degrading the gathered signal. The respective disposition of the sensors should be able to avoid this risk.

From all the above-cited considerations, the optimal respective position for the two sensors is an angle comprised between 40° and 140°, preferably between 80° and 100°, most preferably 90°. This particular disposition allows to set the X-ray imager rapidly and conveniently for both X-ray operator and patient.

Moreover, the present disposition allows to insert a further element, e.g. an optional collimator or a camera taking pictures of the patient undergoing the radiographic acquisition.

The positions of PAN and CBCT sensors on the alternating mechanism, and therefore the distance of the specific sensor from the X-ray source, are opportunely chosen so as to obtain the best radiographic result. The distance between X-ray source and sensor varies with the specific sensor used.

The X-ray imager comprises a base from which a post raises, the post supporting a device capable of vertically moving a C-arm, the C-arm carrying on one side the X-ray source and a primary collimator immediately downstream the X-rays exit, and on the other side two different types of sensors.

In particular, the PAN sensor and the CBCT sensor are arranged on a mechanism alternating the two sensors, bringing the sensor needed for the desired acquisition in the position where it can be hit by X-rays, and at the same time removing from the X-ray path the undesired sensor. When a teleradiography has to be acquired, the alternating mechanism excludes from the X-ray path both PAN and CBCT sensors.

Two different configurations of the X-ray imager are possible: a minimal configuration with a PAN sensor and a CBCT sensor, without teleradiography support. A second optional configuration is a complete X-ray imager, allowing to alternatively obtain panoramic radiographies, CBCT volumetric radiographies images and teleradiography images, and therefore having a support for the teleradiography, too.

Moreover, two distinct embodiments of the X-ray imager performing teleradiography, too, are possible: one simpler and cheaper embodiment wherein one PAN sensor only is present, and this PAN sensor is detached from the PAN support and positioned on the teleradiography support when a teleradiography is to be acquired. In a second, more expensive embodiment, two sensors are present, one PAN sensor and a teleradiography sensor. In this second embodiment, the teleradiography sensor is bigger than the PAN sensor.

The set up of the X-ray imager can be performed before or after the positioning of the patient in the X-ray imager.

BRIEF SUMMARY OF THE DRAWINGS

The present invention will be now described in more detail with the help of the following figures, showing:

FIG. 2a a schematic view of the position of PAN, CBCT and CEPH sensors during a panoramic image acquisition;

FIG. 2b a schematic view of the position of PAN, CBCT and CEPH sensors during a CBCT volumetric radiography acquisition;

FIG. 2c a schematic view of the position of PAN, CBCT and CEPH sensors during a teleradiography image acquisition;

DETAILED DESCRIPTION OF THE INVENTION

Figure 1:
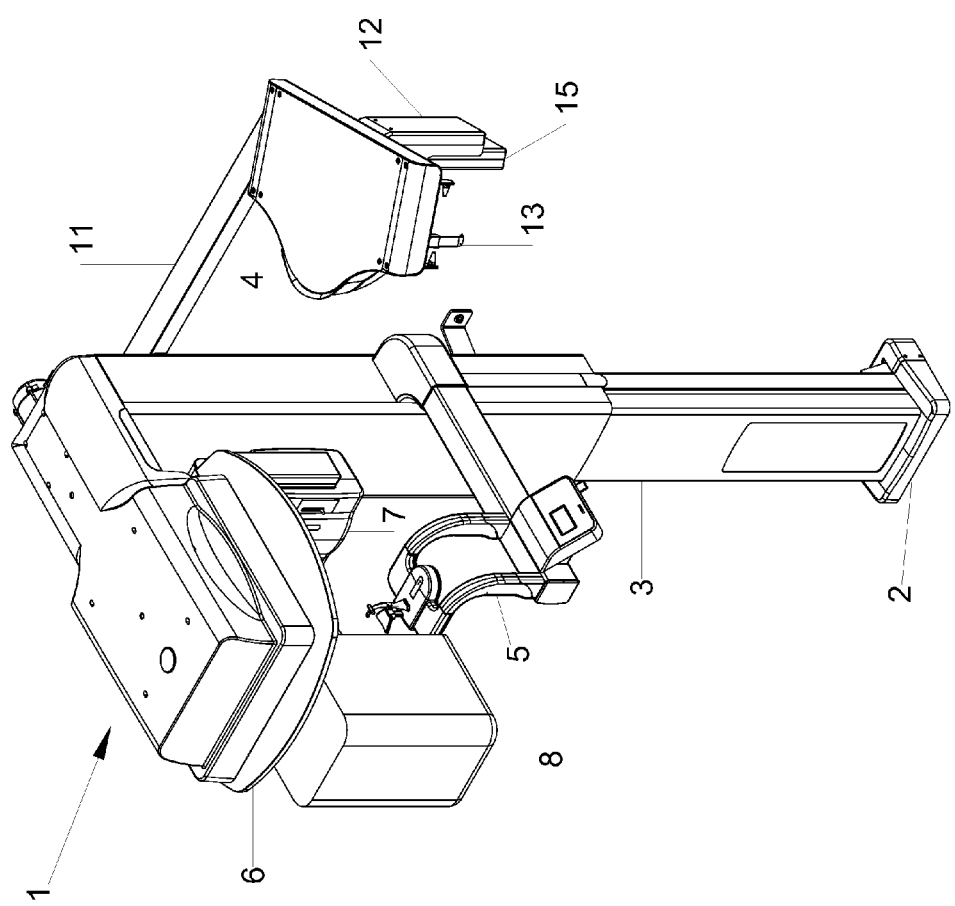
FIG. 1 a prospective view of the complete X-ray imager.

FIG. 1 shows in its entirety an X-ray imager 1, which can alternatively produce panoramic radiographies, CBCT volumetric radiographies and teleradiography images. The imager 1 comprises a base 2 and a post 3 supporting an extension 4, which is provided with a vertical section sliding on the post 3 and a horizontal section. The vertical section of the extension 4 allows the vertical movement of a C-arm 6, which is attached to the horizontal section of the extension 4 and which in its turn supports an X-ray source 7, and a alternating mechanism 8, for alternating the positions of a PAN sensor 9 and a CBCT sensor 10. Moreover, a device 5 for the positioning of the patient is present. On a further optional arm 11, arranged on support 4, a support 12 for CEPH sensor 15 for teleradiography and a further device 13 for positioning the patient are present.

In all acquisition modalities, the X-rays must hit the specific sensor: for radiography acquisition the sensor must be brought in the position allowing the hitting. C-arm 6 has at one of its ends the X-ray source 7, and at its other end the alternating mechanism 8, on which PAN sensor 9 and CBCT sensor 10 are arranged. The alternating mechanism 8 is fixed to C-arm 6 so that it can be moved either manually or automatically exposing the specific sensor needed.

The alternating mechanism 8 has at least two stops, schematically shown in FIGS. 2a, 2b, 2c: one bringing the PAN sensor 9 in the position needed for the acquisition of panoramic images, and one bringing the CBCT sensor 10 in the position needed for the acquisition of CBCT volumetric radiographies. The acquisition can start only when the specific sensor is in the proper stop position. The sensor remains in its stop position for all the acquisition process, and can be moved only after acquisition end.

The positions of PAN sensor 9 and CBCT sensor 10 on alternating mechanism 8, and therefore the distance of the specific sensor from the X-ray source 7 are chosen to get the best radiographic result. The distance between X-ray source 7 and specific sensor varies with the type of sensor used. Generally, the distance between PAN sensor 9 and Xray source 7 is shorter than the distance between CBCT sensor 10 and X-ray source 7.

Compatibly with the magnification degree and the consequent spatial distortion which are held optimal for the kind of acquisition, alternating mechanism 8 is made so that it can bring PAN sensor 9 for the panoramic acquisition at a distance usually comprised between 520 and 580 mm from Xray source 7, while CBCT sensor 10 in CBCT volumetric radiography is positioned at distances usually comprised between 600 and 700 mm from X-ray source 7.

Figure 3A:
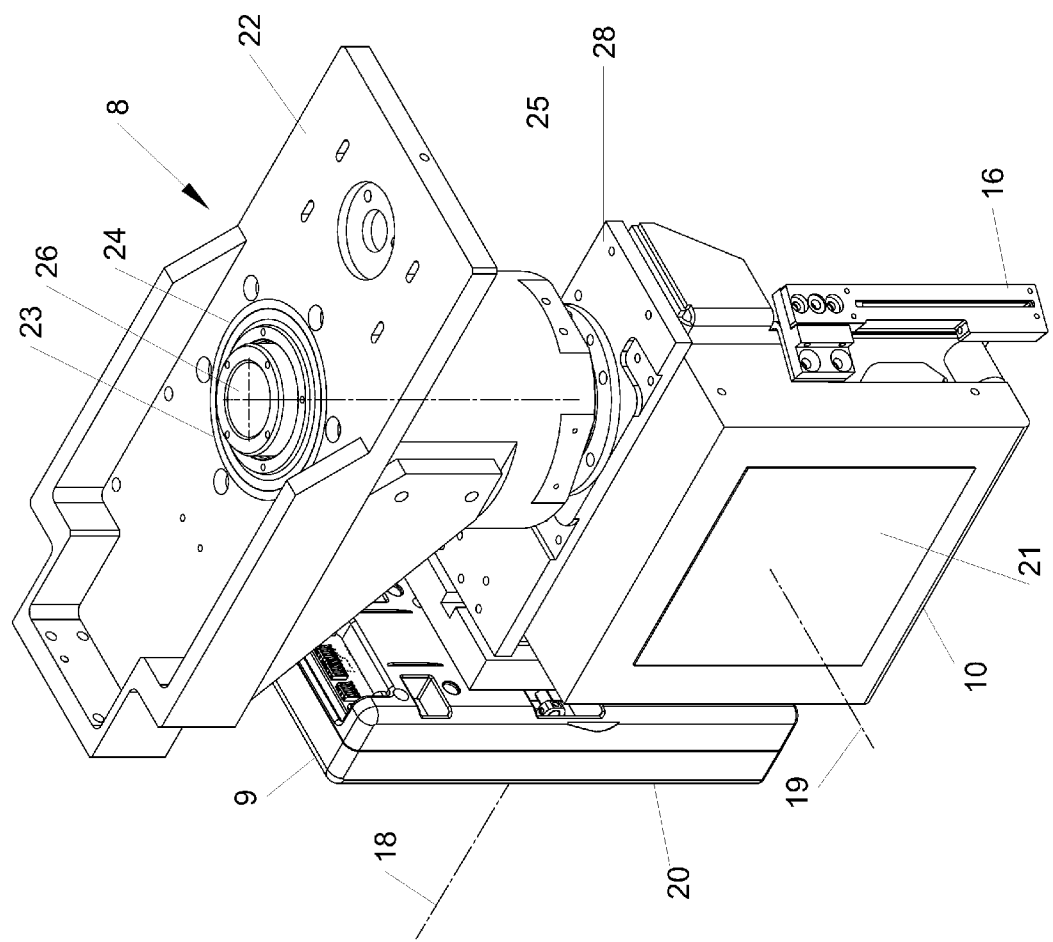
FIG. 3a a perspective view of the mechanism alternating PAN and CBCT sensor.
Figure 3B:
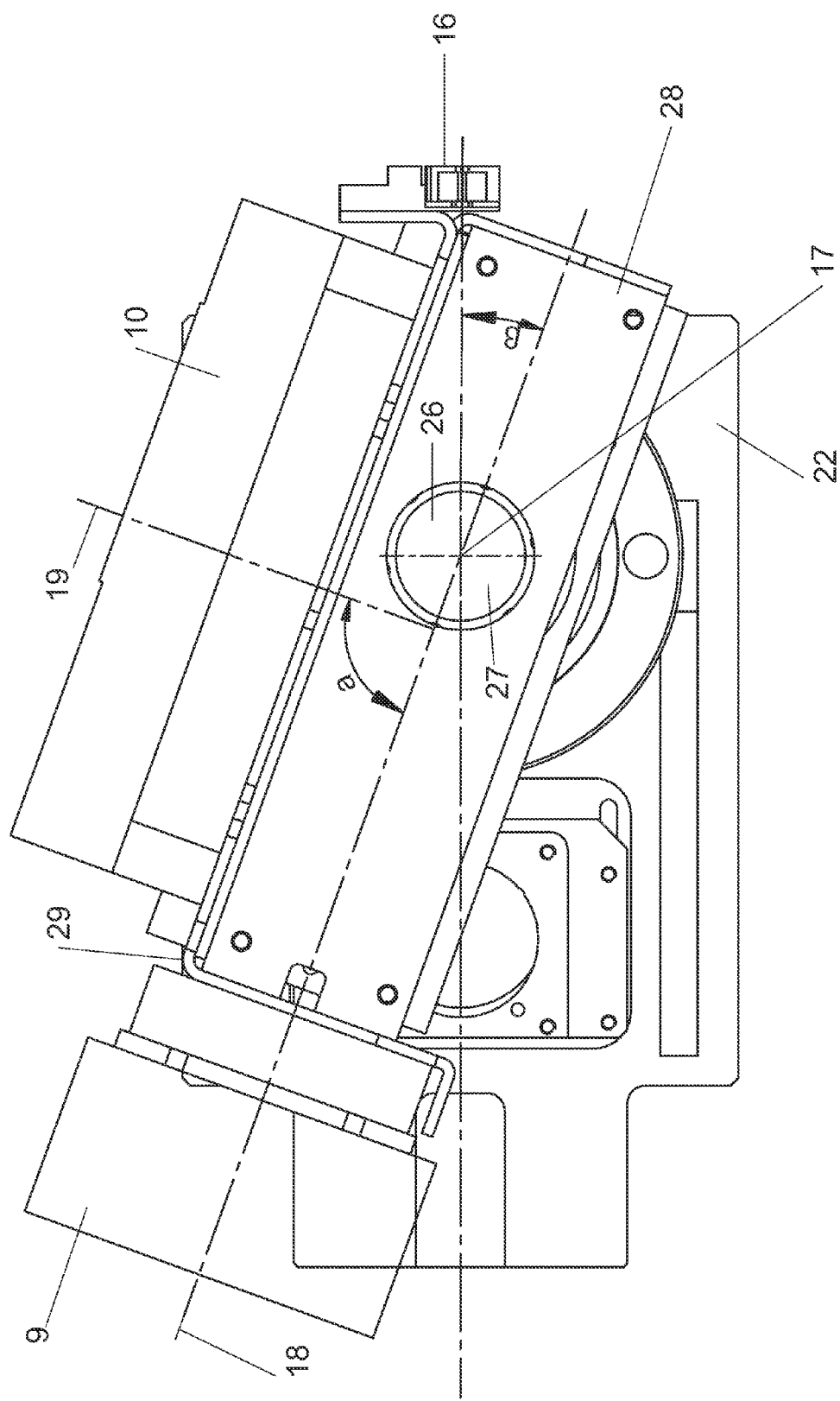
FIG. 3b horizontal section of the mechanism alternating PAN and CBCT sensor.

In cases where the machine comprises an optional secondary collimator 16 mounted on the alternating mechanism 8 for beam collimation during the teleradiographic acquisition, for a good alignment, the distance between X-ray source 7 and CEPH sensor 15 is comprised between 1400 and 1800 mm. Keeping in mind these dimensions, the preferred embodiment of the elements in the alternating mechanism 8, according to the aims of the present invention, and with the aim of optimizing bulk and set up speed, is shown in FIGS. 3a and 3b. FIG. 3a is a perspective view of the alternating mechanism 8, by which the PAN sensor 9, the CBCT sensor 10, and the secondary collimator 16 can be pivoted around a rotation axis 17. FIGS. 3a and 3b further show a PAN sensor axis 18 and CBCT sensor axis 19. The PAN sensor axis 18 and the CBCT sensor axis 19 are centered normals to a sensitive area 20 of the PAN sensor 9 and to a sensitive area 21 of the CBCT sensor 10. In the embodiment depicted in FIGS. 3a and 3b, the PAN sensor axis 18 and the CBCT sensor axis 19 are positioned at an angle a of 90°, respectively; the distance of the photosensitive area 20 of PAN sensor 9 ranges between 220 and 180 mm from the rotation centre 17 of alternating mechanism 8, the distance between the photosensitive area 21 of CBCT sensor 10 and rotation centre 17 ranges between 50 and 130 mm; finally, secondary collimator 16 is at a distance between 80 and 120 mm from the rotation centre 17 of mechanism 8 and positioned at an angle _ ranging between 15° and 25° with respect to the PAN sensor axis 18 of PAN sensor 9. The figures show a preferred embodiment wherein the secondary collimator 16 is placed near the CBCT sensor 10, but this placement is only one of the many embodiments that are possible.

The alternating mechanism 8 may comprises a plate 22, which can be fixed to the arc 6. The plate 22 is provided with a central opening 23, in which a reduced section 24 of a stepper motor 25 is fixed. If the alternating mechanism 8 is mounted on the arc 6, a drive shaft 26 is oriented in a vertical position. At an other end 27 of the drive shaft 26, a plate 28 with a supporting mechanism 29 of the various elements (PAN sensor 9, CBCT sensor 10 and secondary collimator 16) is mounted. Motor actuation can be electronically driven by a microcontroller, and driven when the set up command (for PAN, CBCT or CEPH acquisitions) is sent to the drive circuit. Stop positions can be detected with photoelectric cells, one for each stop position, so that the passage from one configuration to the other can occur without passing from an "initial" position, and counting motor steps necessary to get the desired positions.

On the plate 28, the mechanisms for sensors mounting/demounting can also be present (in the case of an X-ray imager with removable sensors). The plate 28 can also be provided with a mechanism for vertical positioning of the secondary collimator 16 for a correct centring of X-ray beam on CEPH sensor 15.

Alternating mechanism 8 is better shown in FIG. 3b, which represents a horizontal section of the mechanism itself supporting PAN sensor 9, CBCT sensor 10 and optional secondary collimator 16, respectively. This FIG. 3b allows to appreciate the spatial relationship between the two sensors. FIG. 3b shows the rotation axis 17 of the alternating mechanism 8.

When a panoramic acquisition has to be performed, the PAN sensor 9 must be brought on the X-ray path and the primary collimator must be opportunely set. The PAN sensor 9 can be a linear sensor (monodimensional), well known in the art, but also an area sensor (bidimensional). The patient is positioned within the X-ray imager 1 using patient positioning device 5. Once the patient is properly positioned in the X-ray imager 1, the acquisition can start with the emission of X-rays from X-ray source 7.

When a CBCT volumetric radiography has to be performed, the CBCT sensor 10 must be brought on the X-ray path and the primary collimator must be opportunely set. The alternating mechanism 8 rotates, manually or automatically, and the CBCT sensor 10 is brought to intercepts X-rays.

In a particular embodiment, the X-rays emission modality can be modified according to the radiographic acquisition: panoramic acquisitions might be performed with a X-ray continuous emission, while CBCT volumetric radiography might be performed with pulsed X-ray emission, in order to get the best radiographic result with the minimal X-ray dose to the patient.

When a teleradiography acquisition must be performed, the anatomic portion of patient to be imaged must be positioned within support 13, and, if the machine is endowed with a removable sensor only, PAN sensor 9 must be removed from alternating mechanism 8 and positioned on teleradiography support 12, while the primary collimator and the optional secondary collimator 16 must be opportunely set. In a more complete embodiment, wherein the X-ray imager has two sensors 9 and 15, the X-ray imager is ready for the teleradiography acquisition right after patient positioning.

CEPH sensor 15 can be a linear sensor (monodimensional) or an area sensor (bidimensional).

In both cases, alternating mechanism 8 must be positioned so that both PAN sensor 9 and CBCT sensor 10 are excluded from the X-ray path.

On alternating mechanism 8, moreover, a secondary collimator 16 may be present, which must be arranged so as to be crossed by X-rays, therefore stopping the alternating mechanism 8 in a third position. In this case, too, the acquisition can start only when alternating mechanism 8 is in the proper position. This movement can be performed either manually or automatically. Secondary collimator 16 collimates X-rays during teleradiography acquisition, so that the X-ray hits the most precisely possible the sensitive part of the CEPH sensor 15.

Once the X-ray imager 1 is properly set up, teleradiography acquisition can start.

What is claimed is:

1. An apparatus for dental radiography:
    comprising a support (2, 3, 4, 6) allowing motion of an imaging system along predefined trajectories for producing panoramic images and tomographic images of the dentition of a patient,
    the imaging system comprising an X-ray source (7), and a first X-ray sensor (9) for producing the panoramic images, and a second X-ray sensor (10) for producing the tomographic images,
    the first X-ray sensor (9) and the second X-ray sensor (10) being arranged on an alternating mechanism (8) allowing either the first sensor (9) or the second sensor (10) to face the X-ray source (7),
    characterized in that
    the alternating mechanism (8) brings either a first sensor axis (18) of the first sensor (9) or a second sensor axis (19) of the second sensor (10) towards the X-ray radiation source (7) by allowing a pivoting motion around alternation axis (17), wherein the alternating mechanism has at least three detected stop positions, a first detected stop position where the first sensor is in a path of X-rays emitted by the X-ray radiation source (7), a second detected stop position where the second sensor is in a path of X-rays emitted by the X-ray radiation source, and a third detected stop position where the first and second sensors are not in a path of X-rays emitted by the X-ray radiation source, and that
    the first sensor axis (18) and the second sensor axis (19) intersect at an angle ($\alpha$) between about 40° and 140°, if the first sensor axis (18) and the second sensor axis (19) are projected along the alternation axis (17) on a plane perpendicular to the alternation axis (17).

2. The apparatus according to claim 1, wherein the support comprises a base (2) and a post (3), which holds a vertically adjustable extension (4), on which an arm (6) is rotatably mounted, one end of the arm (6) being provided with the X-ray source (7) and the other end of the arm (6) being provided with the alternating mechanism (8) holding the first sensor (9) and the second sensor (10).

3. The apparatus according to claim 1, comprising a further support (11) and a device (13) for positioning a patient during a teleradiography acquisition.

4. The apparatus according to claim 3, wherein the first X-ray sensor (9) for panoramic imaging is relocatable between a position on the alternating mechanism (8) and a position on the further support (11) for teleradiography and is mountable in both positions in a manually detachable way.

5. The apparatus according to claim 4, wherein a third x-ray sensor (15) is arranged on a further support (12) for teleradiography.

6. The apparatus according to claim 1, wherein the X-ray sensors (9, 10) are linear sensors or area sensors.

7. The apparatus according to claim 1, wherein the first sensor (9) is at a distance ranging between 520 and 580 mm from the X-ray source (7) during panoramic imaging, which the second sensor (10) for tomographic imaging is at a distance ranging between 600 and 700 mm from the X-ray source during tomographic imaging.

8. The apparatus according to claim 1, wherein the alternating mechanism (8) further supports a secondary collimator (16).

9. The apparatus according to claim 8, wherein the secondary collimator (16), mounted on the alternating mechanism (8) for the collimation of the X-ray beam, is at a distancing ranging between 1400 and 1800 mm from the X-ray source (7) during teleradiography acquisition.

10. The apparatus according to claim 1, wherein the tomographic imaging is CBCT volumetric radiography.

11. The apparatus according to claim 1, wherein a camera taking pictures of the patient undergoing the radiographic acquisition is arranged on the alternating mechanism (8).

12. The apparatus according to claim 1, wherein the angle ($\alpha$) is between about 80° and 100°.

13. The apparatus according to claim 1, wherein the angle ($\alpha$) is about 90°.

* * * * *